ent [19] [11] 4,032,320
Lush [45] June 28, 1977

[54] SYNERGISTIC HERBICIDAL MIXTURES OF 4-CHLORO-2-OXOBENZOTHIAZOLIN-3-YLACETIC ACID AND 2-METHOXY-3,6-DICHLOROBENZOIC ACID

[75] Inventor: Gerald Bertram Lush, Nottingham, England

[73] Assignee: The Boots Company Limited, Nottingham, England

[22] Filed: Mar. 31, 1975

[21] Appl. No.: 563,718

Related U.S. Application Data

[63] Continuation of Ser. No. 314,571, Dec. 13, 1972, abandoned, which is a continuation of Ser. No. 88,988, Nov. 12, 1970, abandoned, which is a continuation of Ser. No. 770,099, Oct. 23, 1968, abandoned.

[30] Foreign Application Priority Data

Oct. 31, 1967 United Kingdom ............ 49487/67

[52] U.S. Cl. ........................... 71/90; 71/88; 71/107; 71/108; 71/109; 71/110; 71/115; 71/116; 71/117
[51] Int. Cl.$^2$ ........................................ A01N 9/12
[58] Field of Search .............................. 71/90, 115

[56] References Cited

UNITED STATES PATENTS

| | | | |
|---|---|---|---|
| 2,341,868 | 2/1944 | Hitchcock et al. | 71/115 |
| 2,394,916 | 2/1946 | Jones | 71/117 |
| 3,069,429 | 12/1962 | Godson et al. | 71/90 |
| 3,151,970 | 10/1964 | Lush et al. | 71/90 |
| 3,231,362 | 1/1966 | Pfeiffer | 71/115 |
| 3,276,856 | 10/1966 | Esposito | 71/115 |

*Primary Examiner*—Glennon H. Hollrah
*Attorney, Agent, or Firm*—Gordon W. Hueschen

[57] ABSTRACT

Weed control compositions are disclosed which utilize the mixture of 4-chloro-2-oxobenzothiazolin-3-ylacetic acid and 2-Methoxy-3, 6-dichlorobenzoic acid and may contain in addition a third component such as a phenoxyalkanoic acid herbicide.

6 Claims, No Drawings

SYNERGISTIC HERBICIDAL MIXTURES OF 4-CHLORO-2-OXOBENZOTHIAZOLIN-3-YLACETIC ACID AND 2-METHOXY-3,6-DICHLOROBENZOIC ACID

CROSS-REFERENCE TO RELATED APPLICATIONS

This application is a continuation of application Ser. No. 314,571, filed Dec. 13, 1972, which is in turn a continuation of application Ser. No. 088,988, filed Nov. 12, 1970, which is in turn a continuation of application Ser. No. 770,099, filed Oct. 23, 1968, all now abandoned.

The present invention relates to herbicidal compositions and to methods for the control of weeds.

4-Chloro-2-oxobenzothiazolin-3-ylacetic acid is a known herbicide described, for example, in our British Patent Specification No. 862,226. 2-Methoxy-3,6-dichlorobenzoic acid is also a known herbicide described, for example, in British Patent Specification No. 901,553. As is well known in the art, these herbicides may be used as free acids or in the form of salts, esters or amides thereof.

It has now been found that compositions comprising 4-chloro-2-oxobenzothiazolin-3-ylacetic acid or a salt, ester or amide thereof together with 2-methoxy-3,6-dichlorobenzoic acid or a salt, ester or amide thereof have particularly advantageous and unexpected properties in the control of weeds, including the selective control of weeds in cereal crops. For example, it has been found that such compositions give a surprisingly high degree of control of mayweeds (for example *Tripleurospermum maritimum ssp. inodorum* and especially *Anthemis cotula* and *Matricaria spp.* such as *Matricaria recutita* and *Matricaria matricarioides*), and that this degree of control constitutes a synergistic effect.

According to one feature of the present invention there is provided a herbicidal composition comprising, as active ingredients, 4-chloro-2-oxobenzothiazolin-3-ylacetic acid or a salt, ester or amide thereof and 2-methoxy-3,6-dichlorobenzoic acid or a salt, ester or amide thereof.

Typical salts of these herbicidal acids include alkali metal salts such as the potassium and sodium salts, ammonium salts, and salts formed with organic amines. Organic amines which may be used to form salts include those with up to 10 carbon atoms, for example mono-, di- and tri-alkylamines such as ethylamine, dimethylamine, diethylamine, triethylamine, octylamine and 2-ethylhexylamine; mono-, di-, and tri-alkanolamines such as ethanolamine, diethanolamine and triethanolamine, and cyclic amines such as morpholine.

Typical esters of the above-mentioned herbicidal acids include those formed with alcohols with up to 10 carbon atoms, for example alkanols such as methanol, ethanol, propanol, n-butanol, 2-ethylhexanol, 3,5,5-trimethylhexanol and 1-decanol, phenylalkanols such as benzyl alcohol, and alkoxy-substituted alkanols such as 2-butoxyethanol, 2-2'-butoxyethoxyethanol and propylene glycol butyl ether.

Typical amides of the above-mentioned herbicidal acids include the simple unsubstituted amides and those formed with alkylamines with up to 10 carbon atoms.

As used in the description which follows, the term "derivative" designates a salt, ester or amide of a herbicidal acid, including the herbicidal acids hereinbefore described.

In the compositions of the present invention the ratio by weight of 4-chloro-2-oxobenzothiazolin-3-ylacetic acid or derivative thereof to 2-methoxy-3,6-dichlorobenzoic acid or derivative thereof, expressed in terms of the free acids, is generally within the range 1:2 to 10:1, preferably 1:1 to 4:1 and especially 1:1 to 2.5:1.

The compositions of the present invention are particularly valuable for the selective control of weeds in cereal crops. For this purpose, in order to achieve a high level of herbicidal activity against a broader range of weeds, the compositions of the invention preferably include a selective hormone-type phenoxyalkanoic acid herbicide or a derivative thereof, especially 4-chloro-2-methylphenoxyacetic acid, alpha-(4-chloro-2-methylphenoxy)propionic acid, 2,4-dichlorophenoxyacetic acid, alpha-(2,4-dichlorophenoxy)-propionic acid, or a derivative of any of these acids. Typical derivatives of such phenoxyalkanoic acids include those described above for the acids 4-chloro-2-oxobenzothiazolin-3-ylacetic acid and 2-methoxy-3,6-dichlorobenzoic acid.

It has been found that, with compositions of the present invention containing a selective hormone-type phenoxyalkanoic acid herbicide or derivative thereof, optimum results are obtained with a ratio by weight of 4-chloro-2-oxobenzothiazolin-3-ylacetic acid or derivative thereof to 2-methoxy-3,6-dichlorobenzoic acid or derivative thereof, expressed in terms of the free acids, within the range 1:1 to 2.5:1. An especially preferred selective hormone-type phenoxyalkanoic acid herbicide is 4-chloro-2-methylphenoxyacetic acid, and with this acid or a derivative thereof a more preferred weight ratio is within the range 1.3:1 to 1.9:1, especially about 1.5:1.

A suitable ratio by weight of 4-chloro-2-oxobenzothiazolin-3-ylacetic acid to 2-methoxy-3,6-dichlorobenzoic acid to selective hormone-type phenoxyalkanoic acid (or derivatives of each acid), in terms of the free acids, is within the range 1–2.5:1-:3–20, preferably 1–2.5:1:5–15, for the phenoxyacetic acids, gammaphenoxybutyric acids and derivatives thereof and 1–2.5:1:6–40, preferably 1–2.5:1:10–30, for the alpha-phenoxypropionic acids and derivatives thereof.

A particularly preferred embodiment of the present invention is a composition comprising, as active ingredients, 1–2.5 parts 4-chloro-2-oxobenzothiazolin-3-ylacetic acid or a salt thereof, 1 part 2-methoxy-3,6-dichlorobenzoic acid or a salt thereof and 5–15 parts 4-chloro-2-methylphenoxyacetic acid or a salt thereof, the amounts of active ingredients being expressed as parts by weight in terms of the free acids.

The compositions of the present invention may take the form of any of the compositions known in the art of formulating herbicidal compounds. Such compositions may include a diluent or carrier which may be a solid material or a liquid and may comprise a surface active agent. The surface active agent may be, for example, an emulsifying agent, dispersing agent or wetting agent.

The compositions may be compositions in a suitable form for application, or may be primary compositions i.e. concentrated compositions which may be supplied to the user and which require dilution with a suitable quantity of water or other diluent before application. Typical compositions include dispersible powders, dispersible solutions, emulsifiable concentrated solutions, concentrated suspensions, dusts, granular solids, solutions, dispersions and emulsions. The concentration of active ingredients in the primary compositions may vary widely and may be, for example, 5–100% of the composition, depending upon the physical properties of the ingredients. The concentration of active ingredients in the compositions for application to control weeds may be, for example, 0.05–10% w/w.

The compositions of the present invention preferably contain the active ingredients in the form of acids or salts thereof, especially water-soluble salts, for example alkali metal salts or water-soluble amine salts.

According to a further feature of the present invention there is provided a method for the control of weeds which comprises treating the weeds or the soil in which they grow with a herbicidally effective amount of a composition of the present invention as hereinbefore defined. A particular embodiment of this feature is a method for the selective control of weeds in a cereal crop area which comprises treating the crop area with a composition of the present invention as hereinbefore defined, at an application rate sufficient to control the weeds but substantially non-phytotoxic to the crop.

The compositions of the present invention may be applied pre-emergence i.e. prior to the emergence of the weeds, but are generally applied post-emergence i.e. after the emergence of the weeds.

In general, a suitable rate of application of the active ingredients in the compositions of the present invention, expressed in terms of the combined quantity (as free acid) of 4-chloro-2-oxobenzothiazolin-3-ylacetic acid or derivative thereof and 2-methoxy-3,6-dichlorobenzoic acid or derivative thereof will be 0.05–1.5 kg./ha, and often 0.1–0.5 kg./ha. As is well known in the art, this application rate will be influenced by factors such as the species of weeds present, the state of growth of the weeds, and environmental factors. Consideration must also be given to the nature and stage of growth of the crop. For example, in the selective control of weeds in cereal crops, crop areas of spring cereals are generally treated with the compositions of the present invention from the five-leaf stage to the period of jointing, whereas crop areas of winter cereals are generally treated from the stage when the crop is fully tillered to the commencement of jointing.

As hereinbefore mentioned, the compositions of the present invention give an unexpectedly high degree of control of mayweeds, especially *Anthemis cotula* (stinking mayweed) and *Matricaria* spp. such as *Matricaria recutita* (wild chamomile) and *Matricaria matricarioides* (rayless mayweed). In addition, weeds controlled by the compositions of the present invention include *Stellaria media* (chickweed), *Polygonum aviculare* (knotgrass), *Polygonum persicaria* (redshank), *Polygonum convolvolus* (black bindweed) and *Galium aparine* (cleavers).

It is known that, under certain conditions of use, 2-methoxy-3,6-dichlorobenzoic acid (as the free acid or a derivative thereof), when applied to cereals at a rate that is normally not injurious to cereal crops, may have an adverse effect on the cereal crop, causing a reduction in crop yields. It has now surprisingly been found that the addition of 4-chloro-2-oxobenzothiazolin-3-ylacetic acid or a derivative thereof to herbicidal compositions comprising 2-methoxy-3,6-dichlorobenzoic acid or a derivative thereof generally substantially reduces or eliminates this adverse effect on cereal crops. Thus the compositions of the present invention advantageously have a wider safety margin than similar compositions not containing 4-chloro-2-oxobenzothiazolin-3-ylacetic acid or a derivative therof.

The following non-limitative examples illustrate the invention.

EXAMPLE 1

A field trial was carried out in which a plot infested with mayweeds (*Tripleurospermum maritimum* and *Matricaria recutita*) at the young plant stage was divided into rectangular areas which were sprayed at various application rates with aqueous solutions of (A) 4-chloro-2-oxobenzothiazolin-3-ylacetic acid and/or (B) 2-methoxy-3,6-dichlorobenzoic acid, the acids being present in solution in the form of their potassium salts. Each treatment was replicated twice and the degree of weed control obtained was assessed 8 weeks after spraying.

Application rates of compound (A) of 0.41 kg./ha and below gave a poor control of mayweeds. The same effect was obtained with compound (B) at application rates of 0.28 kg./ha and below. However application of a solution containing both compounds at application rates of 0.14 kg./ha for compound (A) and 0.05 kg./ha for compound (B) gave a complete kill of the mayweeds. All application rates are expressed in terms of the free acids.

EXAMPLE 2

An aqueous solution was prepared containing the following ingredients.

| | % w/v |
|---|---|
| 4-Chloro-2-methylphenoxyacetic acid | 22.5 |
| 2-Methoxy-3,6-dichlorobenzoic acid | 1.6 |
| 4-Chloro-2-oxobenzothiazolin-3-ylacetic acid | 2.5 |
| Potassium hydroxide (to pH 8.5–9.0) | |
| Water | to 100 |

This aqueous concentrate was used at an application rate of 5.6 liters concentrate per hectare after dilution with water (1 liter concentrate to 40 liters water) to control weeds in cereal crops. Crop areas of spring barley, spring wheat and spring oats were sprayed overall at growth stages between the 5-leaf stage and the commencement of jointing. Crop areas of winter barley, winter wheat and winter oats were sprayed overall at growth stages between the fully tillered stage and the commencement of jointing. An excellent control of broad-leaved weeds including knotgrass, mayweeds, cleavers, redshank and chickweed was achieved, with no damage to the crops. An almost complete kill of mayweeds (including *Anthemis cotula* and *Matricaria recutita*) was achieved, which is better than would have been expected from the known properties of 4-chloro-2-oxobenzothiazolin-3-ylacetic acid and mixtures of 4-chloro-2-methylphenoxyacetic acid with 2-methoxy-3,6-dichlorobenzoic acid when used as aqueous solutions of their salts at similar application rates.

EXAMPLE 3

Four field trials were carried out. In each trial a crop of winter wheat at a growth stage between the fully tillered stage and the commencement of jointing and heavily infested with *Matricaria recutita* at the young plant stage was divided into rectangular areas which were sprayed with aqueous solutions of the potassium salts of the acids indicated below. Each treatment was replicated twice and the degree of control of *Matricaria recutita*, as % kill, was assessed 8 weeks after spraying. The following results, which are the average of the 4 trials, were obtained. Application rates are expressed as kg./ha, in terms of the free acids.

| Treatment and application rate | % Kill of *M. recutita* |
| --- | --- |
| A, 0.14 | 0 |
| B, 0.09 + C, 1.24 | 61 |
| A, 0.14 + B, 0.09 + C, 1.24 | 95 |

A = 4-chloro-2-oxobenzothiazolin-3-ylacetic acid
B = 2-methoxy-3,6-dichlorobenzoic acid
C = 4-chloro-2-methylphenoxyacetic acid

EXAMPLE 4

An aqueous concentrate was prepared containing the following ingredients (expressed as acid equivalents) in the form of their diethanolamine salts.

| | % w/v |
| --- | --- |
| 4-Chloro-2-oxobenzothiazolin-3-ylacetic acid | 2.5 |
| 2-Methoxy-3,6-dichlorobenzoic acid | 1.6 |
| 4-Chloro-2-methylphenoxyacetic acid | 22.5 |

This concentrate is suitably diluted with water in the ratio of 1:30 to 1:40 by volume to form aqueous solutions suitable for spraying cereal crops.

EXAMPLE 5

A dispersible powder was prepared containing the ingredients listed below. Concentrations of active ingredients are expressed as listed below and not as acid equivalents.

| | % w/w |
| --- | --- |
| 4-Chloro-2-oxobenzothiazolin-3-ylacetic acid, ethyl ester | 5.6 |
| 2-Methoxy-3,6-dichlorobenzoic acid, sodium salt | 3.5 |
| 4-Chloro-2-methylphenoxyacetic acid, sodium salt | 52.0 |
| Sulphite lye | 10.0 |
| Ethylan BCP | 0.5 |
| Colloidal silicic acid | 5.0 |
| Kaolin | to 100.0 |

Ethylan BCP, a proprietary dispersing agent, is an alkylphenolethylene oxide condensate.

On dilution with water, this formulation provides a dispersion of ethyl 4-chloro-2-oxobenzothiazolin-3-ylacetate in an aqueous solution of the sodium salts of the other two active ingredients.

I claim:

1. A herbicidal composition, which is useful in the treatment of Matricaria spp., consisting essentially of an inert carrier and a herbicidally effective amount of an essential synergistic mixture of
    a. an alkali metal salt of 4-chloro-2-oxobenzothiazolin-3-ylacetic acid, and
    b. an alkali metal salt of 2-methoxy-3,6-dichlorobenzoic acid, the amounts being expressed in terms of the free acid in both instances and the weight proportions of (a) and (b) being from 1–2.5:1.

2. A herbicidal composition according to claim 1 comprising 4-chloro-2-oxobenzothiazolin-3-ylacetic acid and 2-methoxy-3,6-dichlorobenzoic acid, both being in the form of their potassium salts.

3. A method for the control of Matricaria spp. in which the locus of the Matricaria spp. is treated with a herbicidally-effective amount of a herbicidal composition as defined in claim 1.

4. A method according to claim 3 for the selective control of Matricaria spp. in a cereal crop area in which the cereal crop is treated with said herbicidal composition at an application rate sufficient to control the Matricaria spp.

5. A method according to claim 4 in which said herbicidal composition is as defined in claim 2.

6. A herbicidal composition, which is useful in the treatment of Matricaria spp., consisting essentially of an inert carrier and a herbicidally effective amount of an essential synergistic mixture of
    a. an alkali metal salt of 4-chloro-2-oxobenzothiazolin-3-ylacetic acid, and
    b. an alkali metal salt of 2-methoxy-3,6-dichlorobenzoic acid, the amounts being expressed in terms of the free acid in both instances and the weight proportions of (a) and (b) being from 1–4:1.

* * * * *